United States Patent [19]

Duncan et al.

[11] Patent Number: 5,123,927
[45] Date of Patent: Jun. 23, 1992

[54] METHOD AND APPARATUS FOR ANTIBIOTIC KNEE PROTHESIS

[75] Inventors: Clive P. Duncan, Vancouver; Martine J. Breault, St-Lambert; Chris P. Beauchamp, Vancouver; Nancy J. Paris, Vancouver; Bassam A. Masri, Vancouver, all of Canada

[73] Assignee: University of British Columbia, Vancouver, Canada

[21] Appl. No.: 764,167

[22] Filed: Sep. 23, 1991

Related U.S. Application Data

[63] Continuation-in-part of Ser. No. 670,905, Mar. 18, 1991.

[30] Foreign Application Priority Data

Dec. 5, 1990 [CA]  Canada ................... 2031571

[51] Int. Cl.$^5$ ............................... A61F 2/38
[52] U.S. Cl. ........................ 623/20; 623/18
[58] Field of Search .............. 623/20, 18, 16; 606/86, 606/92, 99; 264/222, 249, 261, 274, 336

[56]  References Cited

U.S. PATENT DOCUMENTS 3,774,244  11/1973  Walker ........................... 623/20 X
3,882,858   5/1975  Klemm ........................... 623/66 X
3,964,106   6/1976  Hutter, Jr. et al. .............. 623/20
4,191,740   3/1980  Heusser et al. ................. 623/16 X
4,615,705  10/1986  Scales et al. ................... 623/11
4,853,225   8/1989  Wahlig et al. .................. 623/16 X
4,882,149  11/1989  Spector ......................... 623/18 X
5,061,286  10/1991  Lyle ............................. 623/16

Primary Examiner—David J. Isabella
Assistant Examiner—Dinh X. Nguyen
Attorney, Agent, or Firm—C. A. Rowley

[57]  ABSTRACT

A method and equipment for producing an antibiotic loaded knee prothesis by custom molding a femoral prothesis in a removable mold from a settable material containing a selected antibiotic, applying the molded prothesis to the distal end of the femur, completing the set of the material to anchor the prothesis to the femur and removing the removable mold. Next a tibial prothesis is custom molded in a second removable mold from a settable material containing a selected antibiotic, the material set and the so formed tibial prothesis is removed from the second mold and is then connected to the proximal end of the tibia in a position to form an articulating joint with the previously molded and applied femoral prothesis.

12 Claims, 3 Drawing Sheets

METHOD AND APPARATUS FOR ANTIBIOTIC KNEE PROTHESIS

This application is a continuation-in-part of application Ser. No. 07/670,905 filed March 18, 1991.

FIELD OF THE INVENTION

The present inventions relates to a temporary knee prothesis. More particularly the present invention relates to a temporary knee prothesis for permitting articulation of the knee joint while dispensing antibiotic in the proximity of the knee joint.

BACKGROUND OF THE PRESENT INVENTION

Approximately 1.5% of patients undergoing total joint replacement suffer from infection in the joint. These infections must be eradicated and to do so in most cases the joint has to be removed, the infection eliminated or eradicated and subsequently (generally after a substantial period of time) a further or substitute joint is implanted.

The general procedure for eradication of the infection is to remove the joint prothesis and the infected tissue, insert antibiotic loaded cement beads into the cavity so formed and leave the beads in this position for a period of six to twelve weeks or until the infection has been eradicated.

When the infection has been eliminated the inserted cement beads are removed and a new permanent replacement prothesis is implanted.

Obviously in following this procedure during the portion of time (from six to twelve weeks) between the insertion of the antibiotic-loaded beads and until the infection is eradicated the use of the infected limb is severely restricted and the patient usually remains substantially bedridden and confined to hospital over that period.

In treating infected replacement protheses it is also known to use a bone cement impregnated with antibiotic to secure a new permanent prothesis in place without the application of the beads to the cavity i.e. immediately following removal of the previously applied prothesis. Also it is much easier to remove a temporary joint replacement than such a permanent replacement should the treatment be unsuccessful.

SUMMARY OF THE PRESENT INVENTION

It is an object of the present invention to provide a method of applying a temporary total knee joint prothesis for dispensing antibiotic and then to a mold for making such prothesis.

Broadly the present invention relates to a method of treatment of an infected knee joint requiring a knee joint prothesis between a femur and a tibia which comprises removing an implanted knee joint prothesis and infected tissue therearound, custom molding a femoral prothesis having a first bearing means in a first removal mold from a settable material containing a selected antibiotic that may be eluted from said femoral prothesis at a desired rate to combat an infection, at least partially setting said settable material, connecting said femoral prothesis to a distal end of said femur and removing said first mold, custom molding a tibial prothesis having a mating bearing means to cooperate and form an articulated joint with said first bearing means in a second removal mold from said settable material containing said selective antibiotic, setting said material in said second mold to form said tibial prothesis, removing said tibial prothesis from said second mold, connecting said tibial prothesis to a proximal end of said tibia in a position for said first bearing means and said mating bearing means to form an articulated knee joint.

Preferably said settable material will be a bone cement.

Preferably said femoral prothesis is applied to said distal end of said femur before said settable material from which it is molded has set, completing the setting of said settable material so that said settable material bonds (with a weaker bond than if cement per se as opposed to antibiotic cement were used) said femoral prothesis to said distal end of said femur and then removing the first removable mold from said femoral prothesis.

Preferably said method will further comprise embedding a runner forming means into said femoral prothesis, during said molding of said femoral prothesis in a position for said runner means to form said first bearing means.

Preferably said method will also further comprise embedding an insert of material with a low co-efficient of friction into said tibial prothesis during said molding of said tibial prothesis said embedded insert forming said mating bearing means.

The present invention also broadly relates to a set of molds to produce mating femur and tibial prothesis to form a temporary knee joint that dispenses antibiotics to cure infection comprising a first mold having a first interior mold face shaped to form a knee joint forming end of a femur, said first mold including a first mold surface to form a first bearing means in the form of a convex runner on a femoral prothesis formed therein, a second mold, said second mold having a second interior molding face shaped to form a knee joint forming end of a tibia, said second molding face including a second mold surface to form a mating bearing means in a tibial prothesis formed therein, said mating bearing means being shaped to cooperate with said first bearing means to form an articulating knee joint.

Preferably said first mold surface forming said first bearing will comprise a removable insert mounted in said mold, said insert having the required shape to form said first bearing means, means for temporarily positioning said insert in said first mold to permit said insert to separate from said first mold with said femoral prothesis on separation of said femur prosthesis from said first mold.

Preferably said second mold will include a means to position a second removable insert in a position to form said mating bearing means, said second insert being removable from said second mold to remain as a part of said tibial prothesis formed in said second mold.

BRIEF DESCRIPTION OF THE DRAWINGS

Further features, objects and advantages will be evident from the following detailed description of the preferred embodiments of the present invention taken in conjunction with the accompanying drawings in which.

DESCRIPTION OF THE PREFERRED EMBODIMENTS

When a knee prothesis becomes infected to a degree where removal of the prothesis is required the recommended procedure is for the physician to remove the prothesis and cut away the infected tissue. As above indicated, in the prior art techniques, the cavity so formed would then be filled with beads of cement (or water) containing the antibiotic selected by the surgeon or other doctor based on a diagnosis of the particular infection that is causing the problem.

Figure 1:
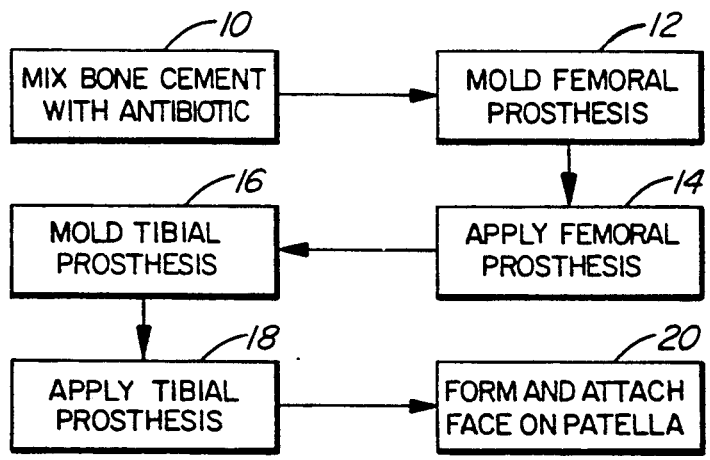
FIG. 1 is a schematic block diagram indicating the main steps of the present invention.

When following the present invention after removal of the infected total knee prothesis and thorough debridement of all infected and necrotic bone, the size of the femur and tibia components are estimated, for example by a trial fit using mold such as those illustrated in FIGS. 3 to 6 inclusive which will be available in various sizes in the operating room. (These molds will be described hereinbelow.) Thereafter a conventional (known) settable bone cement is mixed with the antibiotic as indicated at 10 in FIG. 1 to provide an antibiotic-loaded bone cement, for example, Simplex-P or Palacos bone cement powder may be mixed with the appropriate antibiotic in powder form (provided that the total weight of antibiotics does not exceed about 4.5 grams per 40 grams of bone cement for this particular bone cement as has been found through practice).

If the antibiotic powder is crystalline in nature it is ground up using a mortar and pestle prior to its addition to the cement powder. The cement and antibiotic are then mixed together to thoroughly distribute the antibiotic through the powdered bone cement; thereafter the setting monomer is added and the cement is further mixed until a doughy state is reached. A portion of the cement is then poured into the femoral mold as indicated at 12 to mold the femoral prothesis and preferably prior to hardening of the cement the femur mold with its cement contained therein is applied to distal end of the femur to position the femoral prothesis in particular the bearing forming end of the femoral prothesis. The excess cement is removed and the mold with the partially set cement are held in place without excessive pressure as indicated at 14 until the cement hardens thereby forming the femoral prothesis in situ and simultaneously anchoring it to the proximal end of the femur.

The first of femoral mold is then peeled off to expose the femoral condyles of the femoral prothesis.

In an alternate procedure the femoral prothesis is allowed to cure within the mold before application to the femur. The so formed femoral prothesis is then simply fixed to the distal end of the femur using the same antibiotic impregnated bone cement used to mold the femoral prothesis.

With the femoral prothesis in place, tibial models of different sizes corresponding to the sizes to tibial molds (to be described below) are then used to approximate the thickness required of the tibial prothesis. A trial reduction is performed.

Antibiotic loaded settable bone cement prepared as above described is then poured into the tibial mold to the required depth as estimated to form the tibial prothesis as indicated at 16. After the cement has hardened the tibial prothesis is removed, defects in the tibia are filled with antibiotic loaded bone cement and the tibial prothesis is then cemented in place as indicated at 18.

Depending on the requirements of the particular case being treated, the patella component is then shaped from a small putty of the antibiotic loaded bone cement and is attached to the undersurface of the patella as indicated at 20.

When all the cement has hardened, the stability of joint is confirmed and range of motion checked.

Figure 2:
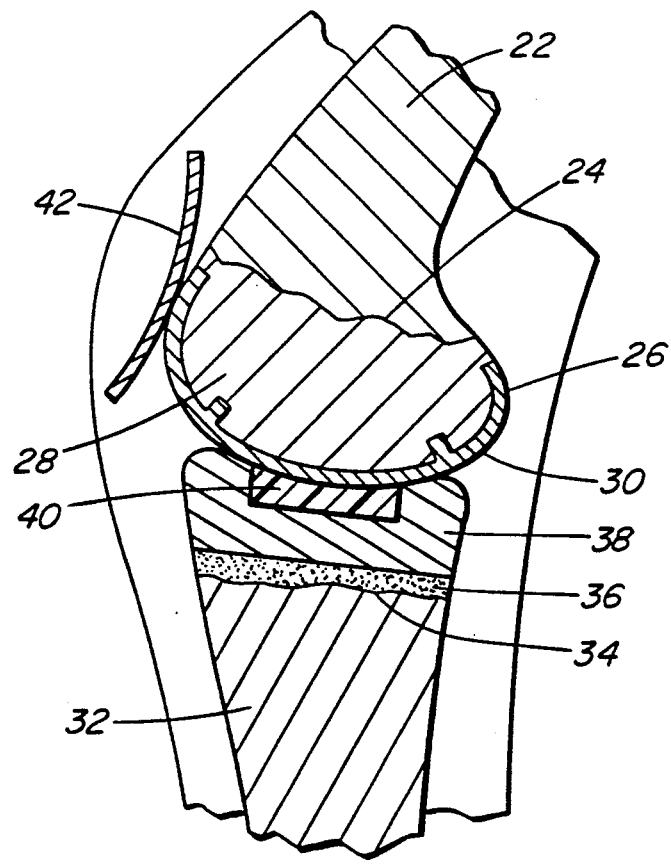
FIG. 2 is a section illustrating a knee joint formed and incorporating the preferred form of the present invention.

The restructure produced as above described is illustrated in FIG. 2, but the illustrated prothesis further includes bearing forming inserts in both the femur and tibial prothesis.

As shown in FIG. 2 the tibia 22 as applied to its adjacent or distal surface 24 a molded femoral prothesis 26 formed primarily from antibiotic loaded bone cement. In the illustrated system the central core and adjoining portions of the femoral prothesis as indicated at 28 are formed by bone cement impregnated with a selected antibiotic and a bearing surface (first bearing means) is provided by a metal implant 30 molded integral with the femoral prothesis and adapted to form the bearing surfaces of the femoral condyles (there are two implants 30 as will be described hereinbelow).

The tibia 32 has a tibial prothesis 38 applied to its adjacent 34 end via a layer of antibiotic loaded cement 36.

In the illustrated arrangement the tibial prothesis 38 as above described is molded from antibiotic loaded bone cement containing the required amount of the selected antibiotic and incorporating a bearing insert 40 which is molded in situ during the formation of the tibial prothesis as will be described hereinbelow. Two such inserts 40 are provided to form the bearing surface of tibial prothesis i.e. each cooperates with its respective of the condyles.

The patella component formed from antibiotic loaded bone cement is schematically illustrated at 42.

Figure 3:
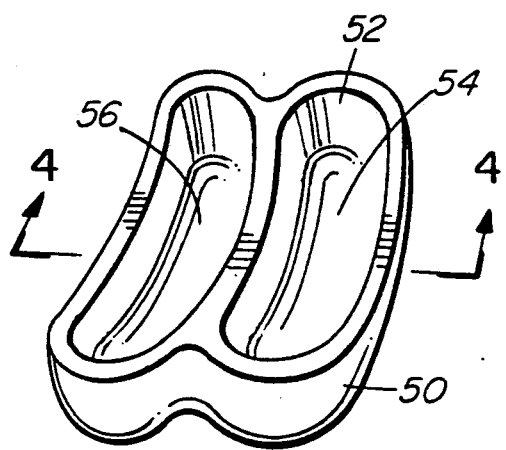
FIG. 3 is an isometric view of a mold for forming a temporary femoral prothesis of the present invention.
Figure 4:
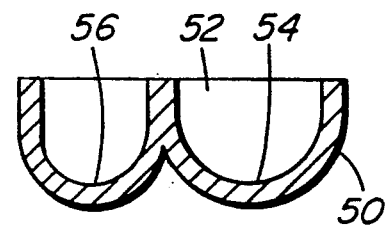
FIG. 4 is a section along the lines 4—4 of FIG. 3.

Referring to FIG. 3 it will be apparent that the mold 50 for forming the femoral prothesis is a simple cavity mold having its inner mold surface 52 contoured to conform with the desired exterior shape of the femoral prothesis. The antibiotic loaded bone cement is simply poured into the mold 50 to the desired height and the cement flows to take on the shape of the mold.

In the illustrated arrangement the femoral mold 50 has a pair of first mold surfaces 54 and 56 to form two condyles of convex configuration adapted to form the first bearing means of the knee joint.

Figure 5:
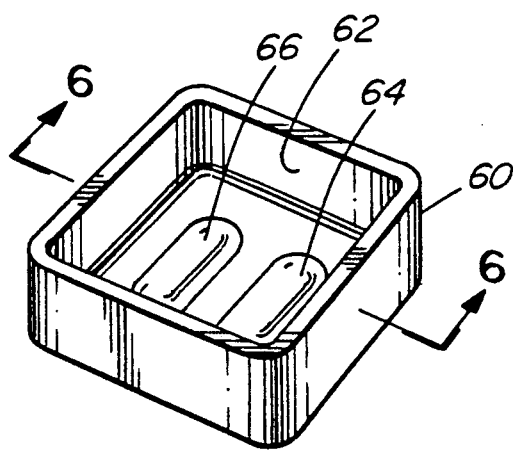
FIG. 5 is an isometric view of a mold for forming a mating tibial prothesis for forming the knee joint.
Figure 6:
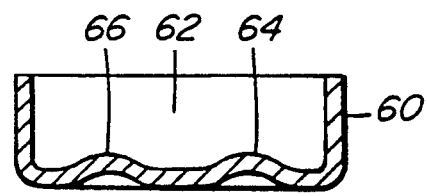
FIG. 6 is a section along the line 6—6 of FIG. 5.

The tibia mold 60 shown in FIGS. 5 and 6 is a suitably shaped mold to define the cooperating end of the tibia. This inner mold face is formed with a pair of indentations on its inner face 62 forming second mold surfaces as indicated at 64 and 66 which are adapted to form a concave bearing surfaces adapted to sliding to receive the condyle portions formed by the surfaces 54 and 56 of the mold 50.

Figure 7:
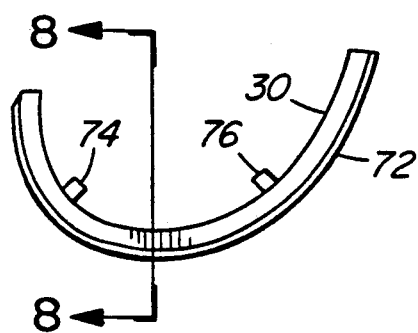
FIG. 7 is a side elevation of a bearing runner insert for use in the femoral prothesis.
Figure 8:
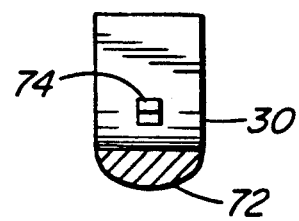
FIG. 8 is a section along the line 8—8 of FIG. 7.

FIG. 7 shows a runner insert 30 adapted to form a condyle in the femoral prothesis. As illustrated the insert 30 is provided with a convex bearing surface 72 that is convex in two planes as illustrated in FIGS. 7 and 8. In the illustrated system a pair of locking tabs 74 and 76 are provided to key the runner 30 into the cement as it sets.

Figure 9:
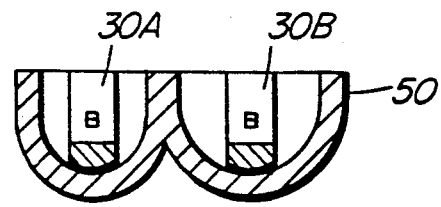
FIG. 9 is a section similar to FIG. 4 but showing a bearing runner insert of FIGS. 7 and 8 incorporated within the mold.

As shown in FIG. 9 these runners 30 may be applied into the mold 50 as indicated at 30A and 30B in FIG. 9 before the mold 50 is filled with the antibiotic loaded bone cement so that the inserts 30A and 30B become embedded in the cement and thereby form part of the femoral prothesis 26, i.e. they separate from the mold 50 and remain with the femoral prothesis anchored in place to form the condyle surface for sliding contact (bearings) on the femoral prothesis. The shape of the runners is matched in the area of the mold in which the runners are requires and this shape of the mold facilitates positioning of and holds the runners or inserts 30 in the mold until the cement sets.

Figure 10:
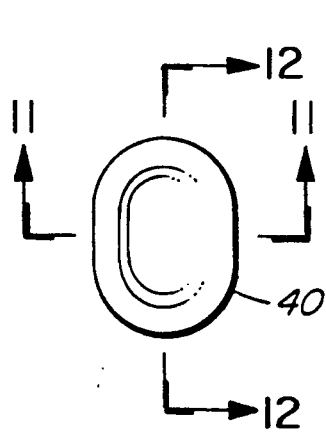
FIG. 10 shows a plan view of a mating bearing forming insert for the tibial prothesis and adapted to form a mating bearing surface on the tibial prothesis.
Figure 11:
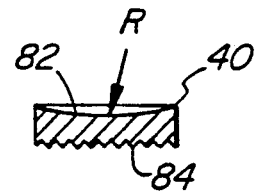
FIGS. 11 and 12 are sections along the lines 11—11 and 12—12 of FIG. 10.
Figure 12:
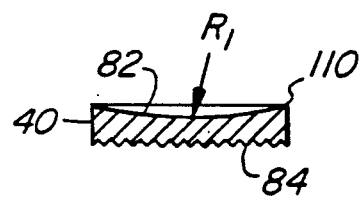
Figure 13:
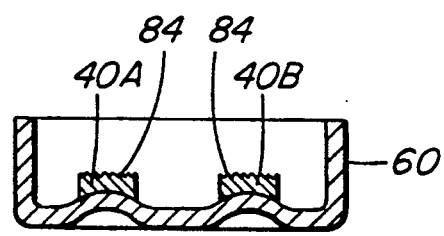
FIG. 13 is a view similar to FIG. 6 showing a pair of mating bearing inserts illustrated in FIGS. 10 to 12 in position in the tibial prothesis forming mold.

FIG. 10 illustrates a bearing insert for the tibial prothesis. As illustrated the inserts 40 are each provided with a bearing surface 82 that is convex in two planes as indicated by the arrows R and $R_1$ in FIGS. 11 and 12. The radius R is slightly larger of the convex surface 72 as illustrated in FIG. 8 and similarly the radius $R_1$ is greater than the radii along the length of the runner 30.

Two inserts 40, as indicated at 40A and 40B are applied to the inside of the mold 60 (see FIG. 12) before the mold is filled with antibiotic loaded bone cement for molding of the tibial prothesis and are positioned by corresponding shapes in the inside surface 82 of the mold 60 as indicated in a position to form the mating bearing surfaces of the resultant tibial prothesis.

In the illustrated arrangement, the side of the inserts 40 remote from the concave side 82 is provided with a roughened surface as indicated at 84 which may be formed by a plurality of up-standing knobs adapted to facilitate keying of the inserts 40 into the bone cement from which the tibial prothesis is made.

Where inserts 30 and 40 are to be applied to the molds 50 and 60 respectively, it is preferred to provide a position edge or cavity into which the inserts 30 or 40 may be positioned to facilitate and ensure that the inserts are properly positioned before the cement is poured into the mold.

Having described the invention, modifications will be evident to those skilled in the art without departing from the spirit of the invention as defined in the appended claims.

We claim:

1. A method of treatment of an infected knee joint requiring a knee joint prothesis between a femur and a tibia which comprises removing an implanted knee joint prothesis and infected tissue therearound, custom molding a femoral prothesis having a first bearing means disposed in a first removable mold, introducing a settable material into said mold, said settable material containing a selected antibiotic that may be elutriated from said femoral prothesis at a desired rate to combat an infection, at least partially setting said settable material, contacting and connecting said femoral prothesis to a distal end of said femur and removing said first mold, custom molding a tibial prothesis having a mating bearing means disposed in a second removable mold, said bearing means adapted to cooperate and form an articulated joint with said first bearing means introducing said settable material containing said selective antibiotic into said second mold, setting said material in said second mold to form said tibial prothesis, removing said tibial prothesis from said second mold, contacting and connecting said tibial prothesis to a proximal end of said tibia in a position for said first bearing means and said mating bearing means to form an articulated knee joint.

2. A method as defined in claim 1 wherein said settable material is bone cement.

3. A method as defined in claim 1 wherein said femoral prothesis is applied to said distal end of said femur before said settable material from which it is molded has set and the setting of said settable material is completed while said femoral prothesis is so applied so that said settable material bonds said femoral prothesis to said proximal end of said femur and then removing the first removable mold from said femoral prothesis.

4. A method as defined in claim 1 further comprising embedding a runner forming means into said femoral prothesis, during said molding of said femoral prothesis in a position for said runner means to form said first bearing means.

5. A method as defined in claim 1 further comprising embedding an insert of material with a low co-efficient of friction into said tibial prothesis during said molding of said tibial prothesis, said embedded insert forming said mating bearing means.

6. A method as defined in claim 2 wherein said femoral prothesis is applied to said distal end of said femur before said settable material from which it is molded has set and the setting of said settable material is completed while said femoral prothesis is so applied so that said settable material bonds said femoral prothesis to said proximal end of said femur and then removing the first removable mold from said femoral prothesis.

7. A method as defined in claim 3 further comprising embedding a runner forming means into said femoral prothesis, during said molding of said femoral prothesis in a position for said runner means to form said first bearing means.

8. A method as defined in claim 3 further comprising embedding an insert of material with a low co-efficient of friction into said tibial prothesis during said molding of said tibial prothesis, said embedded insert forming said mating bearing means.

9. A method as defined in claim 4 further comprising embedding an insert of material with a low co-efficient of friction into said tibial prothesis during said molding of said tibial prothesis, said embedded insert forming said mating bearing means.

10. A method as defined in claim 6 further comprising embedding an insert of material with a low co-efficient of friction into said tibial prothesis during said molding of said tibial prothesis, said embedded insert forming said mating bearing means.

11. A set of molds to produce mating femur and tibial prothesis to form a temporary knee joint that dispenses antibiotics to cure infection comprising a first mold having a first interior mold face shaped to form a knee joint forming end of a femur, said first mold including a first mold surface to form a first bearing means in the form of a convex runner on a femoral prothesis formed therein, said first mold surface forming said first bearing comprising a first removable insert means mounted in said mold, said first insert means having the required shape to form said first bearing means, means for temporarily positioning said first insert means in said first mold to permit said first insert means to separate from said first mold with said femoral prothesis on separation of said femur prosthesis from said first mold, a second mold, said second mold having a second interior molding face shaped to form a knee joint forming end of a tibia, said second molding face including a second mold surface to form a mating bearing means in a tibial prothesis formed therein, said mating bearing means being shaped to cooperate with said first bearing means to form an articulating knee joint.

12. A set of molds as defined in claim 11 wherein said second mold includes a means to position a second removable insert means in a position to form said mating bearing means, said second insert means being removable from said second mold to remain as a part of said tibial prothesis formed in said second mold.

* * * * *